US00PP31373P3

(12) United States Plant Patent
Beginn

(10) Patent No.: US PP31,373 P3
(45) Date of Patent: Jan. 14, 2020

(54) ***LYCHNIS* PLANT NAMED 'IFLYPH'**

(50) Latin Name: *Lychnis flos-cuculi*
Varietal Denomination: IFLYPH

(71) Applicant: Olivier Beginn, Sonsbeck (DE)

(72) Inventor: Olivier Beginn, Sonsbeck (DE)

(73) Assignee: Innoflora Plant Breeding B.V., Heerhugowaard (NL)

( * ) Notice: Subject to any disclaimer, the term of this patent is extended or adjusted under 35 U.S.C. 154(b) by 0 days.

(21) Appl. No.: 16/501,091

(22) Filed: Feb. 21, 2019

(65) Prior Publication Data

US 2019/0357412 P1 Nov. 21, 2019

Related U.S. Application Data

(60) Provisional application No. 62/762,742, filed on May 17, 2018.

(51) Int. Cl.
*A01H 5/02* (2018.01)
*A01H 6/30* (2018.01)

(52) U.S. Cl.
USPC ..... Plt./452

(58) Field of Classification Search
USPC ..... Plt./263.1, 452
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Lychnis* plant named 'IFLYPH', characterized by its relatively compact, upright and uniformly mounded plant habit; freely basal clumping growth habit; moderately vigorous to vigorous growth habit; freely flowering habit; and white-colored double-type flowers arranged in dense inflorescences.

2 Drawing Sheets

Botanical designation: *Lychnis flos-cuculi.*
Cultivar denomination: 'IFLYPH'.

BACKGROUND OF THE INVENTION

The present invention relates to a new and distinct cultivar of *Lychnis* plant, botanically known as *Lychnis flos-cuculi*, typically grown as a container *Lychnis* plant and hereinafter referred to by the name 'IFLYPH'.

The new *Lychnis* plant is a naturally-occurring whole plant mutation of *Lychnis flos-cuculi* 'Lychjenpet', disclosed in U.S. Plant Pat. No. 27,495. The new *Lychnis* plant was discovered and selected by the Inventor as a single plant from within a population of plants of 'Lychjenpet' in a controlled greenhouse environment in Sonsbeek, Germany in June, 2015.

Asexual reproduction of the new *Lychnis* plant by in vitro meristem culture since June, 2016 has shown that the unique features of this new *Lychnis* plant are stable and reproduced true to type in successive generations of asexual reproduction.

SUMMARY OF THE INVENTION

The following traits have been repeatedly observed and are determined to be the unique characteristics of 'IFLYPH'. These characteristics in combination distinguish 'IFLYPH' as a new and distinct *Lychnis* plant:

1. Relatively compact, upright and uniformly mounded plant habit.
2. Freely basal clumping growth habit.
3. Moderately vigorous to vigorous growth habit.
4. Freely flowering habit.
5. White-colored double-type flowers arranged in dense inflorescences.

Plants of the new *Lychnis* differ primarily from plants of the mutation parent, 'Lychjenpet', in flower color as plants of 'Lychjenpet' have bright pink-colored flowers.

Plants of the new *Lychnis* can be compared to plants of unnamed selections of *Lychnis flos-cuculi* known to the Inventor, not patented. In side-by-side comparisons conducted in Sonsbeek, Germany, plants of the new *Lychnis* differ from plants of unnamed selections of *Lychnis flos-cuculi* known to the Inventor in the following characteristics:

1. Plants of the new *Lychnis* are shorter, more compact and denser than plants of unnamed selections of *Lychnis flos-cuculi.*
2. Plants of the new *Lychnis* are more freely flowering than plants of unnamed selections of *Lychnis flos-cuculi.*
3. Flowers of plants of the new *Lychnis* are white in color whereas flowers ofplants of unnamed selections of *Lychnis flos-cuculi* are pink in color.

BRIEF DESCRIPTION OF THE PHOTOGRAPHS

The accompanying colored photographs illustrate the overall appearance of the new *Lychnis* plant showing the colors as true as it is reasonably possible to obtain in colored reproductions of this type. Colors in the photographs may differ slightly from the color values cited in the detailed botanical description which accurately describe the colors of the new *Lychnis* plant.

The photograph on the first sheet is a side perspective view of typical plants of 'IFLYPH' grown in a container.

The photograph at the top of the second sheet is a close-up view of typical flowering stems of 'IFLYPH'.

The photograph at the bottom of the second sheet is a close-up view of typical leaves of 'IFLYPH'.

DETAILED BOTANICAL DESCRIPTION

The aforementioned photographs and following observations, measurements and values describe plants grown during the early summer in 19-cm containers in an outdoor nursery in Heerhugowaard, The Netherlands and under cultural practices typical of commercial *Lychnis* production. During the production of the plants, day temperatures ranged from 10° C. to 25° C. and night temperatures ranged from 4° C. to 15° C. Plants were 15 weeks old when the photographs and the description were taken. In the following description, color references are made to The Royal Horticultural Society Colour Chart, 2015 Edition, except where general terms of ordinary dictionary significance are used.

Botanical classification: *Lychnis flos-cuculi* 'IFLYPH'.

Parentage: Naturally-occurring whole plant mutation of *Lychnis flos-cuculi* 'Lychjenpet', disclosed in U.S. Plant Pat. No. 27,495.

Propagation:

*Type.*—By in vitro meristem culture.

*Time to initiate roots, summer.*—About 15 days at temperatures about 20° C.

*Time to produce a rooted young plant, summer.*—About ten days at temperatures about 15° C. to 20° C.

*Root description.*—Fine, fibrous; close to 156D in color.

*Rooting habit.*—Freely branching; dense.

Plant description:

*Plant and growth habit.*—Herbaceous perennial; basally clumping plant habit with leaves developing from the base; roughly broadly obovate in overall shape; relatively compact, upright and uniformly mounded plant habit; moderately vigorous to vigorous growth habit.

*Plant height, soil level to top of foliar plane.*—About 51 cm.

*Plant height, soil level to top of floral plane.*—About 78 cm.

*Plant diameter or spread.*—About 75.5 cm.

Branch description:

*Branching habit.*—Freely branching habit with about 15 primary branches per plant each primary branch with about eight secondary lateral branches.

*Length.*—About 27.3 cm.

*Diameter.*—About 2 mm.

*Internode length.*—About 12.9 cm.

*Strength.*—Moderately strong.

*Aspect.*—Upright to about 70° from vertical.

*Texture and luster.*—Sparsely to moderately pubescent; slightly rough; slightly glossy.

*Color.*—Close to 143C; at the internodes, close to 143A; color becoming closer to 146D tinged with close to 183D with development.

Leaf description:

*Arrangement.*—Leaves arranged in basal clumps; leaves simple, opposite and sessile.

*Length.*—About 5 cm to 17.5 cm.

*Width.*—About 1.4 cm to 2.1 cm.

*Shape.*—Narrowly oblanceolate to lanceolate; slightly carinate.

*Apex.*—Acute.

*Base.*—Decurrent.

*Margin.*—Entire; slightly and coarsely undulate.

*Texture and luster, upper and lower surfaces.*—Smooth, glabrous; matte.

*Venation pattern.*—Pinnate.

*Color.*—Developing leaves, upper and lower surfaces: Close to 144B. Fully expanded leaves, upper surface: Close to between NN137A and 147A; venation, close to 143C. Fully expanded leaves, lower surface: Close to 147B; venation, close to 144A.

Flower description:

*Flower type and flowering habit.*—Double-type flowers with reproductive organs transformed into petal-like (hereafter described as "petaloids") structures; flowers arranged in compound dichasial cymes on relatively short flowering stems; flowering stems arising from basal clumps, flowering stems mostly erect to somewhat outwardly spreading; flowers face mostly upright to outwardly; each cyme with about eleven flowers and about 1,250 flowers developing per plant over the flowering season; flowers face mostly upright to slightly outwardly.

*Fragrance.*—None detected.

*Time of flowering.*—In Northern Europe, plants flower continuously from spring into the autumn; flowering begins about 15 weeks after planting rooted young plants.

*Flower longevity.*—Individual flowers last about ten days on the plant; flowers persistent.

*Inflorescence length.*—About 9.3 cm.

*Inflorescence width.*—About 8.9 cm.

*Flower diameter.*—About 2.7 cm.

*Flower depth (height).*—About 1.7 cm.

*Flower buds.*—Height: About 7 mm. Diameter: About 3 mm. Shape: Elliptic to oblong. Texture and luster: Smooth, glabrous; matte. Color: Close to 145C slightly tinged with 181D; axillary stripes, close to 146C.

*Petals.*—Quantity and arrangement: About five arranged in a single whorl. Length: About 1.4 cm. Width: About 6 cm. Shape: Spatulate. Apex: Emarginate. Base: Narrowly attenuate. Margin: Entire; moderately undulate. Texture and luster, upper and lower surfaces: Smooth, glabrous; moderately velvety; matte. Color: When opening, upper and lower surfaces: Close to NN155D. Fully opened, upper and lower surfaces: Close to NN155D; color does not change with development.

*Petaloids (transformed reproductive structures).*—Quantity and arrangement: About 50 arranged in about five whorls. Length: About 1.2 cm. Width: About 5 cm. Shape: Spatulate. Apex: Emarginate. Base: Narrowly attenuate. Margin: Entire; moderately undulate. Texture and luster, upper and lower surfaces: Smooth, glabrous; moderately velvety; matte. Color: When opening, upper and lower surfaces: Close to NN155D. Fully opened, upper and lower surfaces: Close to NN155D; color does not change with development.

*Sepals.*—Quantity and arrangement: About five sepals arranged in a single whorl. Length: About 8 mm. Width: About 7 mm. Shape: Lower 75% fused in to a tube; upper 25% deltoid. Apex: Broadly acute. Base: Fused. Margin: Entire. Texture and luster, upper and lower surfaces: Smooth, glabrous; matte. Color: When opening, upper and lower surfaces:

Close to 145D; axillary stripes, close to 146B. Fully opened, upper and lower surfaces: Close to 145D; axillary stripes, close to 146B.

*Peduncles.*—Length: About 13.3 cm. Diameter: About 1 mm. Strength: Moderately strong; flexible. Aspect: Erect to about 30° from vertical. Texture and luster: Sparsely to moderately pubescent; slightly rough; slightly glossy. Color: Close to 143C.

*Pedicels.*—Length: About 1.3 cm. Diameter: About 0.75 mm. Strength: Moderately strong; flexible. Aspect: Erect to about 30° from vertical. Texture and luster: Sparsely to moderately pubescent; slightly rough; slightly glossy. Color: Close to 143A.

*Reproductive organs.*—None observed, all transformed into petal-like structures.

*Seeds and fruits.*—Seed and fruit development has not been observed on plants of the new *Lychnis*; flowers are sterile.

Pathogen & pest resistance: To date, resistance to pathogens and pests common to *Lychnis* plants has not been observed on plants of the new *Lychnis* grown under commercial production conditions.

Garden performance: Plants of the new *Lychnis* have been observed to tolerate rain, wind and temperatures ranging from −23° C. to 40° C.; plants of the new *Lychnis* and to be suitable for USDA Hardiness Zones 5 to 9.

It is claimed:

1. A new and distinct *Lychnis* plant named 'IFLYPH' as illustrated and described.

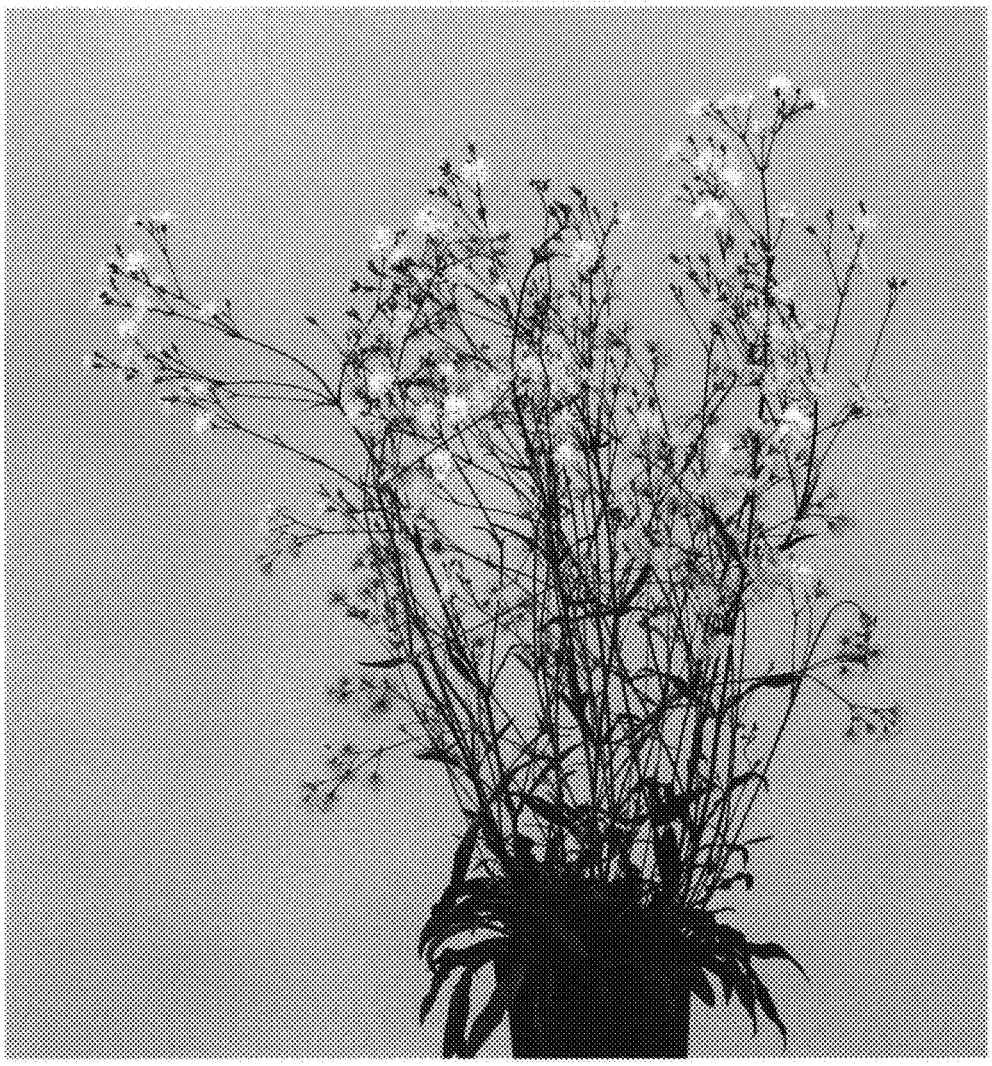

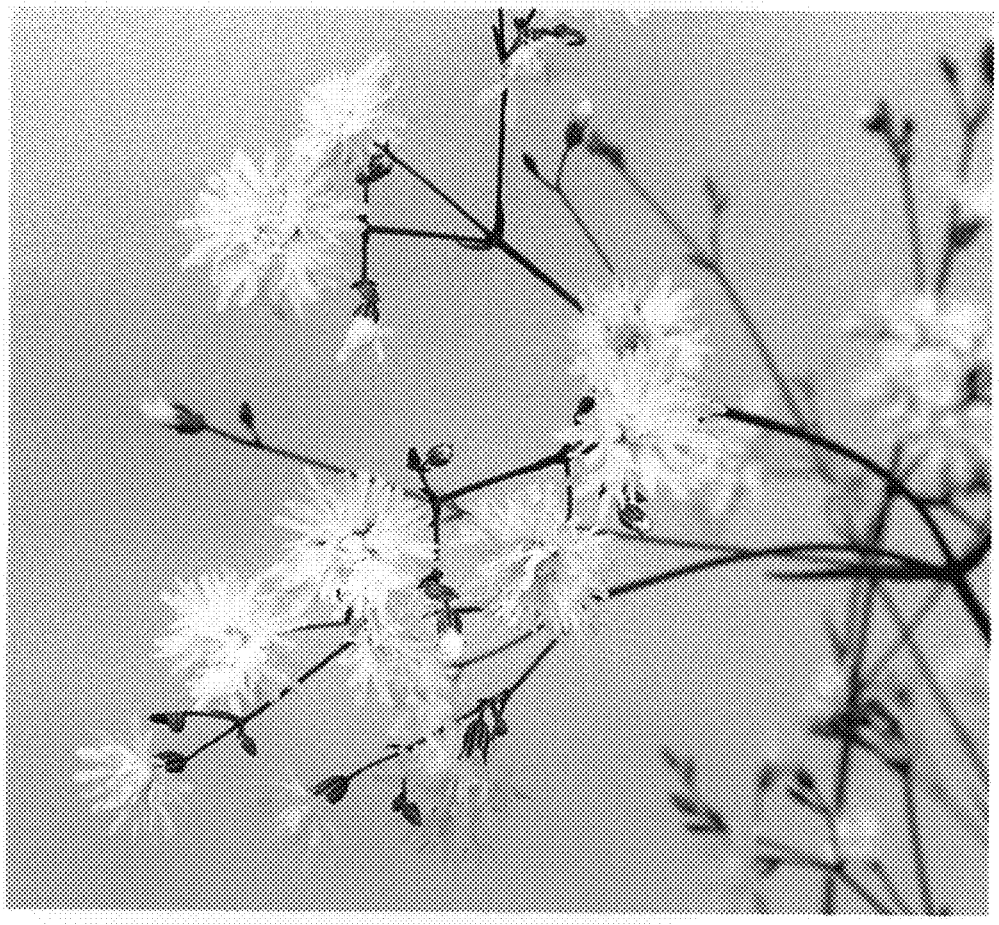
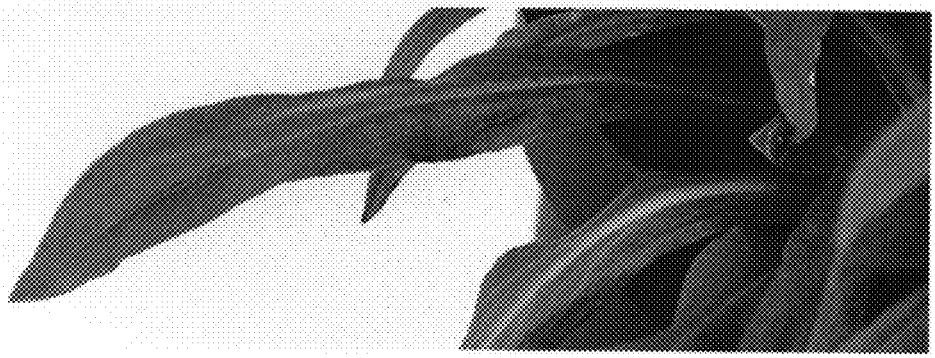

* * * * *